(12) United States Patent
Huang

(10) Patent No.: US 7,288,378 B2
(45) Date of Patent: Oct. 30, 2007

(54) COMPOSITIONS AND METHODS FOR TIGR GENOTYPING ASSAYS

(75) Inventor: Doug Hui Huang, Aliso Viejo, CA (US)

(73) Assignee: Quest Diagnostics Investments Incorporated, Wilmington, DE (US)

( * ) Notice: Subject to any disclaimer, the term of this patent is extended or adjusted under 35 U.S.C. 154(b) by 452 days.

(21) Appl. No.: 10/803,557

(22) Filed: Mar. 17, 2004

(65) Prior Publication Data

US 2005/0095609 A1     May 5, 2005

Related U.S. Application Data

(63) Continuation of application No. 10/017,870, filed on Dec. 12, 2001, now Pat. No. 6,727,354.

(51) Int. Cl.
    *C12Q 1/68*      (2006.01)
    *C12P 19/34*     (2006.01)

(52) U.S. Cl. ..................... 435/6; 435/91.1; 435/91.2

(58) Field of Classification Search ................ 435/6, 435/91.1, 91.2
See application file for complete search history.

(56) References Cited

U.S. PATENT DOCUMENTS

| | | | |
|---|---|---|---|
| 5,861,497 A | 1/1999 | Nguyen et al. | |
| 5,916,778 A | 6/1999 | Stone et al. | |
| 6,171,788 B1 * | 1/2001 | Nguyen et al. | 435/6 |
| 6,248,867 B1 | 6/2001 | Nguyen et al. | |
| 6,403,307 B1 * | 6/2002 | Stone et al. | 435/6 |

OTHER PUBLICATIONS

Brezin et al., "Founder effect in GLC1A-linked familial open-angle glaucoma in Northern France." Am. J. Med. Genet., 76: 438-45, 1998.
Dolnik, "DNA sequencing by capillary electrophoresis (review)." J Biochem Biophys Methods, 41:103-19, 1999.
Dovichi and Zheng, "DNA sequencing by capillary array electrophoresis." Methods Mol Biol, 167:225-39, 2001.
Fahy et al., "Multiplex fluorescence-based primer extension method for quantitative mutation analysis of mitochondrial DNA and its diagnostic application for Alzheimer's disease." Nucleic Acid Research, 25: 3102-3109, 1997.
Hafner et al., "Isothermal amplification and multimerization of DNA by *Bst* DNA polymerase." Biotechniques, Apr 30(4):852-867, 2001.
Heller, "Principles of DNA separation with capillary electrophoresis." Electrophoresis 22:629-43, 2001.
Lindblad-Toh et al., "Large-scale discovery and genotyping of single-nucleotide polymorphisms in the mouse." Nature Genet., (24):381-6., 2000.
Meldrum, "Automation for Genomics, Part One: Preparation for Sequencing." Genome Research, 10:1081-1092, 2000.
Meldrum, "Automation for Genomics, Part Two: Squencers, Microarrays, and Future Trends." Genome Research, 10:1288-1303, 2000.
Mitchelson, "Application of capillary electrophoresis for DNA polymorphism analysis." Keith R. Mitchelson and Jing Cheng eds., *Methods in Molecular Biology*, Totowa, NJ: Humana Press, 2001, pp. 3-26.
Morisette et al., "Homozygotes carrying an autosomal dominant *TIGR* mutation do not manifest glaucoma." Nat. Genet., 19:319-321, 1998.
Nguyen et al., "Gene structure and properties of TIGR, an olfactomedin-relatred glycoprotein cloned from glucocorticoid-induced trabecular meshwork cells." J. Biol. Chem., 273: 6341-50, 1998.
Saiki, "Amplification of Genomic DNA." Innis et al., Eds., *PCR Protocols: A Guide to Methods and Applications*. San Diego, CA: Academic Press, 1990, pp. 13-20.
Shimizu et al., "Age-dependent prevalence of mutations at the *GLC1A* locus in primary open-angle glaucoma." Am. J. Ophthalmol., 130:165-77, 2000.
Wharam et al., "Specific detection of DNA and RNA targets using a novel isothermal nucleic acid amplification assay based on the formation of a three-way junction structure." Nucleic Acids Res., 29(11):E54-E54, 2001.

* cited by examiner

*Primary Examiner*—Kenneth R. Horlick
(74) *Attorney, Agent, or Firm*—Foley & Lardner, LLP

(57) ABSTRACT

Methods and compositions are described for use in the rapid and simultaneous screening of one or more samples for one or more polymorphisms in the TIGR gene. The methods and compositions of the present invention can be used to rapidly determine if polymorphisms in a gene encoding the TIGR protein are present in the genome of a subject. Identifying which polymorphisms are present in an individual can permit the diagnosis or prediction of the risk of glaucoma in the subject.

14 Claims, 2 Drawing Sheets

Figure 1: TIGR/Myocilin's exon 3 SEQ ID NO: 9

```
   1    atcattgtc tgtgtttgga aagattatgg attaagtggt gcttcgtttt cttttctgaa
  61    tttaccagga tgtggagaac tagtttgggt aggagagcct ctcacgctga aacagcaga
 121    aacaattact ggcaagtatg gtgtgtggat gcgagacccc aagcccacct accccctacac
 181    ccaggagacc acgtggagaa tcgacacagt tggcacggat gtccgccagg ttttgagta
 241    tgacctcatc agccagttta tgcagggcta cccttctaag gttcacatac tgcctaggcc
 301    actggaaagc acgggtgctg tggtgtactc ggggagcctc tatttccagg gcgctgagtc
 361    cagaactgtc ataagatatg agctgaatac cgagacagtg aaggctgaga aggaaatccc
 421    tggagctggc taccacggac agttcccgta ttcttggggt ggctacacgg acattgactt
 481    ggctgtggat gaagcaggcc tctgggtcat ttacagcacc gatgaggcca aggtgccat
 541    tgtcctctcc aaactgaacc agagaatct ggaactcgaa caaacctggg agacaaacat
 601    ccgtaagcag tcagtcgcca atgccttcat catctgtggc accttgtaca ccgtcagcag
 661    ctacacctca gcagatgcta ccgtcaactt tgcttatgac acaggcacag gtatcagcaa
 721    gaccctgacc atcccattca gaaccgcta taagtacagc agcatgattg actacaaccc
 781    cctggagaag aagctctttg cctgggacaa cttgaacatg gtcacttatg acatcaagct
 841    ctccaagatg tgaaaagcct ccaagctgta caggcaatgg cagaaggaga tgctcagggc
 901    tcctgggggg agcaggctga agggagagcc agccagccag gcccaggca gctttgactg
 961    ctttccaagt tttcattaat ccagaaggat gaacatggtc accatctaac tattcaggaa
1021    ttgtagtctg agggcgtaga caatttcata taataaatat cctttatctt ctgtcagcat
1081    ttatgggatg tttaatgaca tagttcaagt tttcttgtga tttggggcaa aagctgtaag
1141    gcataatagt ttcttcctga aaaccattgc tcttgcatgt tacatggtta ccacaagcca
1201    caataaaaag cataacttct aaaggaagca gaatagctcc tctggccagc atcga
```

Figure 2: TIGR/Myocilin's promoter sequence SEQ ID NO: 10

```
   1    agcgcagggg aggagaagaa aagagaggga tagtgtatga gcaagaaaga cagattcatt
  61    caagggcagt gggaattgac cacagggatt atagtccacg tgatcctggg ttctaggagg
 121    cagggctata ttgtgggggg aaaaaatcag ttcaagggaa gtcgggagac ctgatttcta
 181    atactatatt tttcctttac aagctgagta attctgagca agtcacaagg tagtaactga
 241    ggctgtaaga ttacttagtt tctccttatt aggaactctt tttctctgtg gagttagcag
 301    cacaagggca atcccgtttc ttttaacagg aagaaaacat tcctaagagt aaagccaaac
 361    agattcaagc ctaggtcttg ctgactatat gattggtttt ttgaaaaatc atttcagcga
 421    tgtttactat ctgattcaga aaatgagact agtacccttt ggtcagctgt aaacaaacac
 481    ccatttgtaa atgtctcaag ttcaggctta actgcagaac caatcaaata agaatagaat
 541    ctttagagca aactgtgttt ctccactctg gaggtgagtc tgccagggca gtttggaaat
 601    atttacttca caagtattga cactgttgtt ggtattaaca acataaagtt gctcaaaggc
 661    aatcattatt tcaagtggct taaagttact tctgacagtt ttggtatatt tattggctat
 721    tgccatttgc ttttgtttt ttctctttgg gtttattaat gtaaagcagg gattattaac
 781    ctacagtcca gaaagcctgt gaatttgaat gaggaaaaaa ttacattttt gttttacca
 841    ccttctaact aaatttaaca ttttattcca ttgcgaatag agccataaac tcaaagtggt
 901    aataacagta cctgtgattt tgtcattacc aatagaaatc acagacattt tatactatat
 961    tacagttgtt gcagatacgt tgtaagtgaa atatttatac tcaaaactac tttgaaatta
1021    gacctcctgc tggatcttgt ttttaacata ttaataaaac atgtttaaaa ttttgatatt
1081    ttgataatca tatttcatta tcatttgttt cctttgtaat ctatatttta tatatttgaa
1141    aacatctttc tgagaagagt tccccagatt tcaccaatga ggttcttggc atgcacacac
1201    acagagtaag aactgattta gaggctaaca ttgacattgg tgcctgagat gcaagactga
1261    aattagaaag ttctcccaaa gatacacagt tgttttaaag ctagggtga ggggggaaat
1321    ctgccgcttc tataggaatg ctctccctgg agcctggtag ggtgctgtcc ttgtgttctg
1381    gctggctgtt attttttctct gtccctgcta cgtcttaaag gacttgtttg gatctccagt
1441    tcctagcata gtgcctggca cagtgcaggt tctcaatgag tttgcagagt gaatgaaat
1501    ataaactaga aatatatcct tgttgaaatc agcacaccag tagtcctggt gtaagtgtgt
1561    gtacgtgtgt gtgtgtgtgt gtgtgtgtgt gtaaaaccag gtggagatat aggaactatt
1621    attggggtat gggtgcataa attgggatgt tcttttttaaa aagaaactcc aaacagactt
1681    ctggaaggtt attttctaag aatcttgctg gcagcgtgaa ggcaaccccc ctgtgcacag
1741    ccccacccag cctcacgtgg ccacctctgt cttccccat gaagggctgg ctccccagta
1801    tatataaacc tctctggagc tcgggcatga gccagcaagg ccacccatcc aggcacctct
1861    cagcacagca gagcttttcca gaggaagcct caccaagcct ctgcaatgag gttcttctgt
1921    gcacgttgct gcagctttgg gcctgagatg ccagctgtcc agctgctgct tctggcctgc
1981    ctggtgtggg atgtggggc caggacagct cagctcagga aggccaatga ccagagtggc
2041    cgatgccagt ataccttcag tgtggccagt cccaatgaat ccagctgccc agagcagagc
2101    caggccatgt cagtcatcca taacttacag agagacagca gcacccaacg cttagacctg
2161    gaggccacca aagctcgact cagctccctg gagagcctcc tccaccaatt gaccttggac
2221    caggctgcca ggccccagga gacccaggag gggctgcaga gggagctggg cacctgagg
2281    cgggagcggg accagctgga aacccaaacc agagagttgg agactgccta cagcaacctc
2341    ctccgagaca agtcagttct ggaggaagag aagaagcgac taaggcaaga aaatgagaat
2401    ctgccagga ggttggaaag cagcagccag gaggtagcaa ggctgagaag gggccagtgt
2461    ccccagaccc gagacactgc tcgggctgtg ccaccaggct ccagagaagg taagaatgca
2521    gagtgggggg actctgagtt cagcaggtga tatggctcgt agtgacctgc tacaggcgct
2581    ccaggcctcc ctgcctgccc tttctcctag agactgcaca gctagcacaa gacagatgaa
2641    ttaaggaaag cacagcgatc accttcaagt attactagta atttagctcc tgagagcttc
2701    atttagatta gtggttcaga gttcttgtgc ccctccatgt cagttttcac agtccatagc
2761    aaaaggagaa ataaaaggac cgggtgagat gtgtctgcat
```

US 7,288,378 B2

SEQUENCE LISTING

<160> NUMBER OF SEQ ID NOS: 14

<210> SEQ ID NO 1
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 1
cgaatagagc cataaactca aagtggtaat aa                32

<210> SEQ ID NO 2
<211> LENGTH: 22
<212> TYPE: DNA
<213> ORGANISM: Artificial Sequence
<220> FEATURE:

<223> OTHER INFORMATION: Description of Artificial Sequence: Primer

<400> SEQUENCE: 2
ccgtattctt ggggtggcta ca                                          22

<210> SEQ ID NO 3
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 3
ctcaaacctg ggagacaaac atccgt                                      26

<210> SEQ ID NO 4
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 4
gactgctata agtacagcag catgattgac tacaa                            35

<210> SEQ ID NO 5
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 5
gcggtcccaa aagggtcagt gtatggtgtg tggatgcgag                       40

<210> SEQ ID NO 6
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 6
gcggtcccaa aagggtcagt aagttgtccc aggcaaagag                       40

<210> SEQ ID NO 7
<211> LENGTH: 41
<212> TYPE: DNA
<213> ORGANISM: Artificial Sequence
<220> FEATURE:
<223> OTHER INFORMATION: Description of Artificial Sequence: Primer

<400> SEQUENCE: 7
gcggtcccaa aagggtcagt gcgaatagag ccataaactc a                     41

<210> SEQ ID NO 8
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 8
gcggtcccaa aagggtcagt atctggggaa ctcttctcag                       40

<210> SEQ ID NO 9
<211> LENGTH: 1255
<212> TYPE: DNA
<213> ORGANISM: Homo sapiens

<400> SEQUENCE: 9

| | | | | | |
|---|---|---|---|---|---|
| gatcattgtc | tgtgtttgga | aagattatgg | attaagtggt | gcttcgtttt | cttttctgaa | 60 |
| tttaccagga | tgtggagaac | tagtttgggt | aggagagcct | ctcacgctga | aacagcaga | 120 |
| aacaattact | ggcaagtatg | tgtgtgtggat | gcgagacccc | aagcccacct | acccctacac | 180 |
| ccaggagacc | acgtggagaa | tcgacacagt | tggcacggat | gtccgccagg | ttttgagta | 240 |
| tgacctcatc | agccagtttta | tgcagggcta | cccttctaag | gttcacatac | tgcctaggcc | 300 |
| actggaaagc | acgggtgctg | tggtgtactc | ggggagcctc | tatttccagg | gcgctgagtc | 360 |
| cagaactgtc | ataagatatg | agctgaatac | cgagacagtg | aaggctgaga | aggaaatccc | 420 |
| tggagctggc | taccacggac | agttcccgta | ttcttggggt | ggctacacgg | acattgactt | 480 |
| ggctgtggat | gaagcaggcc | tctgggtcat | ttacagcacc | gatgaggcca | aggtgccat | 540 |
| tgtcctctcc | aaactgaacc | cagagaatct | ggaactcgaa | caaacctggg | agacaaacat | 600 |
| ccgtaagcag | tcagtcgcca | atgccttcat | catctgtggc | accttgtaca | ccgtcagcag | 660 |
| ctacacctca | gcagatgcta | ccgtcaactt | tgcttatgac | acaggcacag | gtatcagcaa | 720 |
| gaccctgacc | atcccattca | agaaccgcta | taagtacagc | agcatgattg | actacaaccc | 780 |
| cctggagaag | aagctctttg | cctgggacaa | cttgaacatg | gtcacttatg | acatcaagct | 840 |
| ctccaagatg | tgaaaagcct | ccaagctgta | caggcaatgg | cagaaggaga | tgctcagggc | 900 |
| tcctgggggg | agcaggctga | agggagagcc | agccagccag | ggcccaggca | gctttgactg | 960 |
| cttttccaagt | tttcattaat | ccagaaggat | gaacatggtc | accatctaac | tattcaggaa | 1020 |
| ttgtagtctg | agggcgtaga | caatttcata | taataaatat | cctttatctt | ctgtcagcat | 1080 |
| ttatgggatg | tttaatgaca | tagttcaagt | tttcttgtga | tttgggggcaa | aagctgtaag | 1140 |
| gcataatagt | ttcttcctga | aaaccattgc | tcttgcatgt | tacatggtta | ccacaagcca | 1200 |
| caataaaaag | cataacttct | aaaggaagca | gaatagctcc | tctggccagc | atcga | 1255 |

<210> SEQ ID NO 10
<211> LENGTH: 2800
<212> TYPE: DNA
<213> ORGANISM: Homo sapiens

<400> SEQUENCE: 10

| | | | | | |
|---|---|---|---|---|---|
| agcgcagggg | aggagaagaa | aagagaggga | tagtgtatga | gcaagaaaga | cagattcatt | 60 |
| caagggcagt | gggaattgac | cacagggatt | atagtccacg | tgatcctggg | ttctaggagg | 120 |
| cagggctata | ttgtggggggg | aaaaaatcag | ttcaaggaa | gtcgggagac | ctgatttcta | 180 |
| atactatatt | tttcctttac | aagctgagta | attctgagca | agtcacaagg | tagtaactga | 240 |
| ggctgtaaga | ttacttagtt | tctccttatt | aggaactctt | tttctctgtg | gagttagcag | 300 |
| cacaagggca | atcccgtttc | ttttaacagg | aagaaaacat | tcctaagagt | aaagccaaac | 360 |
| agattcaagc | ctaggtcttg | ctgactatat | gattggtttt | ttgaaaaatc | atttcagcga | 420 |
| tgtttactat | ctgattcaga | aaatgagact | agtacccttt | ggtcagctgt | aaacaaacac | 480 |
| ccatttgtaa | atgtctcaag | ttcaggctta | actgcagaac | caatcaaata | agaatagaat | 540 |
| ctttagagca | aactgtgttt | ctccactctg | gaggtgagtc | tgccagggca | gtttggaaat | 600 |
| atttacttca | caagtattga | cactgttgtt | ggtattaaca | acataaagtt | gctcaaaggc | 660 |

-continued

```
aatcattatt tcaagtggct taaagttact tctgacagtt ttggtatatt tattggctat      720
tgccatttgc ttttgtttt ttctctttgg gtttattaat gtaaagcagg gattattaac      780
ctacagtcca gaaagcctgt gaatttgaat gaggaaaaaa ttacatttt gtttttacca      840 ccttctaact aaatttaaca ttttattcca ttgcgaatag agccataaac tcaaagtggt      900
aataacagta cctgtgattt tgtcattacc aatagaaatc acagacattt tatactatat      960
tacagttgtt gcagatacgt tgtaagtgaa atatttatac tcaaaactac tttgaaatta     1020
gacctcctgc tggatcttgt ttttaacata ttaataaaac atgtttaaaa ttttgatatt     1080
ttgataatca tatttcatta tcatttgttt cctttgtaat ctatatttta tatatttgaa     1140
aacatctttc tgagaagagt tccccagatt tcaccaatga ggttcttggc atgcacacac     1200
acagagtaag aactgattta gaggctaaca ttgacattgg tgcctgagat gcaagactga     1260
aattagaaag ttctcccaaa gatacacagt tgttttaaag ctaggggtga ggggggaaat     1320
ctgccgcttc tataggaatg ctctccctgg agcctggtag ggtgctgtcc ttgtgttctg     1380
gctggctgtt attttctct gtccctgcta cgtcttaaag gacttgtttg gatctccagt     1440
tcctagcata gtgcctggca cagtgcaggt tctcaatgag tttgcagagt gaatggaaat     1500
ataaactaga aatatatcct tgttgaaatc agcacaccag tagtcctggt gtaagtgtgt     1560
gtacgtgtgt gtgtgtgtgt gtgtgtgtgt gtaaaaccag gtggagatat aggaactatt     1620
attggggtat gggtgcataa attgggatgt tcttttaaa aagaaactcc aaacagactt     1680
ctggaaggtt attttctaag aatcttgctg gcagcgtgaa ggcaaccccc ctgtgcacag     1740
ccccacccag cctcacgtgg ccacctctgt cttcccccat gaagggctgg ctccccagta     1800
tatataaacc tctctggagc tcgggcatga gccagcaagg ccacccatcc aggcacctct     1860
cagcacagca gagctttcca gaggaagcct caccaagcct ctgcaatgag gttcttctgt     1920
gcacgttgct gcagctttgg gcctgagatg ccagctgtcc agctgctgct tctggcctgc     1980
ctggtgtggg atgtgggggc caggacagct cagctcagga aggccaatga ccagagtggc     2040
cgatgccagt ataccttcag tgtggccagt cccaatgaat ccagctgccc agagcagagc     2100
caggccatgt cagtcatcca taacttacag agagacagca gcacccaacg cttagacctg     2160
gaggccacca aagctcgact cagctccctg gagagcctcc tccaccaatt gaccttggac     2220
caggctgcca ggccccagga gacccaggag gggctgcaga gggagctggg caccctgagg     2280
cgggagcggg accagctgga aacccaaacc agagagttgg agactgccta cagcaacctc     2340
ctccgagaca agtcagttct ggaggaagag aagaagcgac taaggcaaga aaatgagaat     2400
ctggccagga ggttggaaag cagcagccag gaggtagcaa ggctgagaag gggccagtgt     2460
ccccagaccc gagacactgc tcgggctgtg ccaccaggct ccagagaagg taagaatgca     2520
gagtgggggg actctgagtt cagcaggtga tatggctcgt agtgacctgc tacaggcgct     2580
ccaggcctcc ctgcctgccc tttctcctag agactgcaca gctagcacaa gacagatgaa     2640
ttaaggaaag cacagcgatc accttcaagt attactagta atttagctcc tgagagcttc     2700
atttagatta gtggttcaga gttcttgtgc ccctccatgt cagttttcac agtccatagc     2760
aaaaggagaa ataaaaggac cgggtgagat gtgtctgcat                           2800
```

<210> SEQ ID NO 11
<211> LENGTH: 36
<212> TYPE: DNA
<213> ORGANISM: Artificial Sequence
<220> FEATURE:
<223> OTHER INFORMATION: Description of Artificial Sequence: Synthetic

```
                                    -continued
         oligonucleotide

<400> SEQUENCE: 11
ccggggtggt tggcgaaggc agtcccctgt gctgcc                                    36

<210> SEQ ID NO 12
<211> LENGTH: 36
<212> TYPE: DNA
<213> ORGANISM: Artificial Sequence
<220> FEATURE:
<223> OTHER INFORMATION: Description of Artificial Sequence: Synthetic
         oligonucleotide

<400> SEQUENCE: 12
ccggagtggt tggcgaaggc agtcccctgt gctgcc                                    36

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence: Synthetic
         oligonucleotide

<400> SEQUENCE: 13
aggtgactgc cttcgccaac cac                                                  23

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: Synthetic
         oligonucleotide

<400> SEQUENCE: 14
aggtgactgc cttcgccaac cact                                                 24
```

COMPOSITIONS AND METHODS FOR TIGR GENOTYPING ASSAYS

CROSS-REFERENCE TO RELATED PATENT APPLICATIONS

This application is a Continuation of U.S. application Ser. No. 10/017,870, now issued U.S. Pat. No. 6,727,354, filed Dec. 12, 2001, incorporated herein by reference in its entirety.

FIELD OF THE INVENTION

The invention relates to the field of diagnostic assays and assays for identifying patients at risk for development of glaucoma.

BACKGROUND OF THE INVENTION

The following description of the background of the invention is provided simply as an aid in understanding the invention and is not admitted to describe or constitute prior art to the invention.

Glaucoma is the second most common cause of blindness in the United States. It is estimated that some two million Americans have glaucoma, with half of those suffering unaware of the presence of the disease. Primary open-angle glaucoma ("POAG") is the most common form of glaucoma, accounting for some 60 to 70% of all glaucomas.

POAG is characterized by obstruction of the normal aqueous outflow of fluids through the trabecular meshwork, canal of Schlemm, intrascleral channels, and episcleral and conjunctival veins. In open-angle glaucoma, this obstruction exists despite an angle that appears open. Generally, a patient that has not been otherwise diagnosed as having glaucoma first becomes aware of the disease due to losses in the visual field. By this point, the degree of optic nerve atrophy resulting from the disease may be quite severe, and is irreversible. Thus, early diagnosis and treatment play a key role in patient management.

Several risk factors have been identified as being related to POAG, including elevated intraocular pressure ("IOP," 50% of patients present with an IOP of <22 mm Hg), increased age (POAG is 6× more common in persons >60 years of age), a family history of the disease (a 15× increased chance of developing glaucoma), race (African Americans are at an increased risk for more serious disease), diabetes, hypertension, myopia, and the use of corticosteroids.

While elevated IOP is a primary risk factor for development of POAG, about ⅙ of patients exhibit an IOP within the normal range. Additionally, there is currently no reliable method for predicting which patients presenting with elevated IOP will progress to POAG. Recently, the relationship of the trabecular meshwork-inducible glucocorticoid response ("TIGR") gene and protein have been studied for possible associations with glaucoma and related diseases. See, e.g., U.S. Pat. Nos. 5,861,497, 5,916,778, 5,925,748, and 6,248,867; Morissette et al., Nat. Genet. 19: 319-21 (1998); Brezin et al., Am. J. Med. Genet. 76: 438-45 (1998); Shimizu et al., Am. J. Ophthalmol. 130: 165-77 (2000); Nguyen et al., J. Biol. Chem. 273: 6341-50 (1998); and Lindblad-Toh et al., Nat. Genet. 24: 381-6 (2000). Each publication and patent in the foregoing section is hereby incorporated by reference in its entirety, including all tables, figures, and claims.

SUMMARY OF THE INVENTION

The present invention is drawn to methods and compositions for the screening of samples for one or more TIGR polymorphisms. The sample can be a biological sample, such as a sample from a subject. The invention can be used to determine which of a plurality of TIGR polymorphisms are present in the genome of a subject. Preferably, a plurality of different samples are assayed, each in its own individual reaction mixture, and/or several different polymorphisms in the TIGR gene are assayed in that single reaction mixture. Thus, a plurality of samples may be simultaneously assayed for several different TIGR polymorphisms in a single cycle (batch run) of the assay.

In a first aspect, the invention provides methods of testing for the presence of one or more polymorphisms of a TIGR gene, in one or more samples comprising TIGR nucleic acids, by generating a labeled nucleic acid that provides a means of identifying a particular polymorphism, thus distinguishing that polymorphism from other polymorphisms that might be present in the same gene. The particular polymorphism may be identified, for example, by determining both the length of the labeled nucleic acid and the identity of a distinctively labeled nucleotide incorporated at an end of the nucleic acid.

In preferred embodiments, these methods comprise one or more of the following steps: (a) preparing a reaction mixture that contains (i) sample nucleic acid suspected of containing a TIGR nucleic acid sequence, (ii) a nucleic acid polymerase, (iii) one or more extension primers, wherein the extension primers comprise nucleotide sequences that terminate at positions located one nucleotide 3' from the positions of one or more preselected polymorphism(s) of interest, and (iv) one or more labeled dideoxynulceotide triphosphates, or ddNTPs; (b) incubating the reaction mixture under conditions such that extension primers that hybridize to the TIGR nucleic acids are labeled by addition of one of the ddNTPs comprising a label to the 3'-end of the detection primer, in order to generate one or more labeled oligonucleotides; and (c) detecting a signal from the labeled oligonucleotides. The presence of a specific polymorphism can be identified by the presence of a distinctive signal at a position in the sequence of the extended nucleic acid.

In certain embodiments, TIGR nucleic acid obtained from a sample is amplified to provide an amount of TIGR nucleic acid sufficient for primer extension to determine the presence or absence of one or more polymorphic forms of TIGR in the original sample. While the exemplary methods described hereinafter relate to amplification using the polymerase chain reaction ("PCR"), numerous other methods are known in the art for amplification of nucleic acids (e.g., isothermal methods, rolling circle methods, etc.). The skilled artisan will understand that these other methods may be used either in place of, or together with, PCR methods.

The phrase "TIGR nucleic acid" refers to any nucleic acid containing sequences directly associated with production of the TIGR protein, including TIGR genomic DNA, TIGR-encoding hnRNA, mature TIGR-encoding mRNA, or amplification products thereof. Any TIGR nucleic acid may be the subject of the methods described herein. In certain embodiments for example, a TIGR RNA may be reverse transcribed into DNA, and the DNA subjected to the analysis methods described hereinafter. In preferred embodiments, the methods are applied to TIGR gene sequences.

The phrases "TIGR gene sequences," "TIGR genomic DNA," and "TIGR gene" as used herein refer to the nucleic acid unit present in the genome of an animal, preferably a human, encoding the TIGR protein, and includes both the TIGR coding sequence and the upstream enhancer and promoter regions operably associated with the TIGR coding sequence in the genome.

The term "biological sample" as used herein refers to a sample obtained from a biological source, e.g., an organism, cell culture, tissue sample, etc. A biological sample can, by way of non-limiting example, consist of or comprise blood, sera, urine, feces, epidermal sample, skin sample, cheek swab, sperm, amniotic fluid, cultured cells, bone marrow sample and/or chorionic villi. Convenient biological samples may be obtained by, for example, scraping cells from the surface of the buccal cavity.

The term "subject" as used herein refers to any eukaryotic organism. Preferred subjects are fungi, invertebrates, insects, arachnids, fish, amphibians, reptiles, birds, marsupials and mammals. A mammal can be a cat, dog, cow, pig, horse, ox, elephant, simian. Most preferred subjects are humans. A subject can be a patient, which refers to a human presenting to a medical provider for diagnosis or treatment of a disease. The term "animals" includes prenatal forms of animals, such as fetuses.

As used herein, a "plurality of samples" refers to at least two. Preferably, a plurality refers to a relatively large number of samples. A plurality of samples is from about 5 to about 500 samples, preferably about 25 to about 200 samples, most preferably from about 50 to about 200 samples. Samples that are processed in a single batch run of the method of the invention are usually prepared in plates having 24, 48, 96, 144, or 192 wells. The term "samples" includes samples per se as well as controls, standards, etc. that are included in a batch run.

A "preselected TIGR polymorphism" is a TIGR nucleic acid sequence that has been selected for testing by the methods of the invention. Examples of preselected TIGR polymorphisms include wild type TIGR, and single base polymorphisms referred to herein as MT-1 (a promoter mutation), and T377M, E423K, and N480K (all exon 3 mutations). The MT-1 mutation replaces C with G at position 906 in the promoter sequence of TIGR (FIG. 2). The T377M mutation replaces C with T at position 468 in the TIGR coding sequence, leading to a substitution of Thr with Met in the TIGR protein; the N480K mutation replaces C with A at position 778 in the TIGR coding sequence, leading to a substitution of Asn with Lys in the TIGR protein; and the K423E mutation replaces A with G at position 605 in the TIGR coding sequence, leading to a substitution of Lys with Glu in the TIGR protein (FIG. 1).

The assays described herein can be used to rapidly determine which of a selected group of polymorphic TIGR nucleic acid forms are present in a sample comprising TIGR nucleic acid. By "rapid" it is meant that the length of time that is taken to carry out a single batch run of the assay, from the moment a reaction mixture comprising nucleic acid is prepared to the moment a signal can be detected, is from about 1 second to about 10, 15 or 30 seconds, about 1, 5, 10 or 30 minute(s), or 1, 3, 5, 8, 24 or 48 hour(s). When samples are from multiple subjects, the assays can be used to determine the TIGR genotype of each subject.

By "distinctively labeled", it is meant that each type of member of a set is labeled with a label that can be distinguished from the labels used for other members of the set. For example, in a set of distinctively labeled nucleotides (e.g., dideoxy NTPs, or ddNPTs), each type of "N" (nucleotide) is labeled with a label that can be distinguished from the other types of labels. Thus, for example, if four labels designated 1, 2, 3, and 4 are used to label the four types of ddNTPs, each ddATP molecule is labeled with label "*1", each ddTTP molecule is labeled with label "*2", each ddCTP molecule is labeled with label "*3", and each ddGTP molecule is labeled with label "*4". In some aspects of the invention, the distinctive label is a fluorescent label.

The skilled artisan will understand that, if one wishes to determine if a specific genotype is present in a sample, e.g., a "T" in a position in the TIGR sequence that would be a "G" in the wild-type sequence, one need only provide a single labeled ddNTP, in this case ddTTP, with an appropriate extension primer. If the "T" polymorphism is present, the labeled ddTTP will be incorporated into the 3' end of the extension primer. In contrast, if the wild-type sequence is present, no labeled extension primer will be created. Depending on the polymorphisms selected for analysis, from one to four labeled ddNTPs may be required to perform an assay. One may also choose to include all four ddNTPs in a reaction for convenience, or so that even wild-type sequences become labeled.

As used herein, "primer extension" refers to the enzymatic extension of the three-prime (3') hydroxy group of an extension primer, which is an oligonucleotide that is paired in a duplex to a template nucleic acid. For an example of primer extension as applied to the detection of polymorphisms, see Fahy et al., Mutliplex fluorescence-based primer extension method for quantative mutation analysis of mitrochondrial DNA and its diagnostic application for Alzheimer's disease, Nucleic Acid Research 25:3102-3109, 1997. The extension reaction is catalyzed by a DNA polymerase. By "DNA Polymerase" it is meant a DNA polymerase, or a fragment thereof, that is capable of catalyzing the addition of bases to a primer sequence in a sequence-specific fashion. A DNA polymerase can be an intact DNA polymerase, a mutant DNA polymerase, an active fragment from a DNA polyerase, such as the Klenow fragment of E. coli DNA polymerase, and a DNA polymerase from any species, including but not limited to thermophilic organisms.

Extension of the 3' end of the oligonucleotide generates an oligonucleotide having a length greater than the extension primer and having a sequence that is the reverse complement of the template nucleic acid. If one of the nucleotides in the added sequence is labeled, then the extended oligonucleotide becomes labeled.

Preferably, an extension primer has a nucleotide sequence that binds in a complementary fashion to a portion of a nucleic acid sequence that encodes or modulates the expression of the TIGR gene, or to the complement of such a sequence. Extension primers must be of a length sufficient to provide specific binding to the target sequence of interest. Such primers comprise an exact complement to the sequence of interest for 15 to 75 nucleotides in length, preferably 17 to 50 nucleotides in length, and more preferably from 20 to 30 nucleotides in length. The extension primer sequence has a 3' terminus that pairs with a nucleotide base that is, in the sample nucleic acid to which the primer is hybridized, 5' from the site of one or more bases in the sequence of interest that represent a polymorphism in a gene. Suitable extension primers are described herein, and may be one of the sequences set forth in SEQ ID NOS:1-4.

In addition to the sequence that ensures hybridization to the target site, an extension primer may have additional nucleotides added to the 5' end that need not participate in specific binding. Thus, such primers may extend for 15 to 75 nucleotides in length, preferably 17 to 50 nucleotides in length, and more preferably from 20 to 30 nucleotides in length, only a subset of which is an exact complement to the sequence of interest. In these embodiments, the exact complement may extend for at least 15 nucleotides, more preferably for at least 17 nucleotides, and most preferably for at least 20 nucleotides to ensure specific hybridization of the extension primer. Thus, an extension primer may contain one of the sequences set forth in SEQ ID NOS:1-4 at the 3' end, with additional nucleotides at the 5' end which may or may not be complementary to the TIGR sequence of interest.

In the following diagram of a primer extension reaction, four different ddNTPs, each distinctively labeled, are present in the reaction mixture as designated by dd(A*1)TP, dd(T*2)TP, dd(C*3)TP and dd(G*4)TP, where *1, *2, *3 and *4 represent different labels. In the diagram, the polymorphism in the nucleic acid being tested is indicated by an underlined nucleotide, and the extension primer sequence is italicized. Only one ddNTP, ddTTP, can be added to the 3' end of the extension primer, because thymine (T) is the only base that pairs with adenosine (A). The addition of the dd(T*2)TP to the 3' of the primer prevents any further primer extension because it is a dideoxy, chain-terminating ddNTP. Thus, the only primer that is 3' extended is labeled with label *2. Detection of the signal from label *2 indicates that the A polymorphism is present in the sample:

```
wild-      5'-CCGGGGTGGTTGGCGAAGGCAGTCCCCTGTGCTGCC-3'
type sample     5'-CCGGAGTGGTTGGCGAAGGCAGTCCCCTGTGCTGCC-3'
              ||||||||||||||||||||||||
primer           3'-CACCAACCGCTTCCGTCAGTGGA-5' labeled ddNTP dd(A*¹)TP        3'-CACCAACCGCTTCCGTCAGTGGA-5' dd(T*²)TP        3'-*²TCACCAACCGCTTCCGTCAGTGGA-5' dd(C*³)TP        3'-CACCAACCGCTTCCGTCAGTGGA-5' dd(G*⁴)TP        3'-CACCAACCGCTTCCGTCAGTGGA-5'
```

As discussed herein, an amount of nucleic acid sufficient for primer extension can, but need not be, prepared by amplification, e.g., via PCR using amplification primers. As a non-limiting example, appropriate amplification primers include, but are not limited to, those having sequences set forth in SEQ ID NOS:5-9.

For each reaction mixture, the amount of the nucleic acid sufficient for primer extension can be determined by obtaining a sample comprising nucleic acid and determining the concentration of nucleic acid therein. One skilled in the art will be able to prepare such samples to a concentration and purity necessary to practice the invention, and to estimate the amount of a specific sample that should be added to a particular reaction mixture. A failure to detect a signal in the method of the invention may signify that, among other things, an inadequate amount of nucleic acid has been added to a reaction mixture. Those skilled in the art will be able to trouble-shoot failed batch runs and adjust the contents of the reaction mixtures and/or conditions of the run accordingly. Control samples, both positive and negative, can be included in the batch runs to confirm that appropriate amounts of nucleic acid are present.

One or more of steps of the assays described herein, in any combination, are preferably performed in an automated fashion, typically using robotics, in order to provide for the processing of a large number of samples in a single batch run. Preferred forms of automation will provide for the preparation and separation of a plurality of labeled nucleic acids in small volumes. The term "small volumes" refers to volumes of liquids less than 2 ml, e.g., any volume from about 0.001 picoliters or about 0.001 μl, to any volume about 2 ml, 500 μl, 200 μl, 100 μl, 10 μl, 1 μl, 0.1 μl, 0.01 μl, or 0.001 μl.

The set of distinctively labeled oligonucleotides generated by the methods described herein can be separated from each other so that each is mobilized in a manner that relates to each of their specific positions in the respective nucleotide sequence, and the detection of the distinctive signals generated from the distinctively labeled oligonucleotides occurs during or after the mobilization. Members of the set of distinctively labeled oligonucleotides can be separated from each other so that each is mobilized by electrophoresis. A preferred form of electrophoresis is capillary electrophoresis, but any form of electrophoresis that allows for the separation of a plurality of labeled nucleic acids in small volumes by automated or semi-automated methods and devices may be used.

In additional aspects of the present invention, polymorphic forms of TIGR assayed according to the invention can be used to diagnose subjects suffering from glaucoma or to identify subjects that are at increased risk for developing glaucoma. In preferred embodiments, such subjects may also exhibit one or more additional risk factors for glaucoma, including elevated IOP ($\geq$22 mm Hg, more preferably 22-30 mm Hg, most preferably 27-30 mm Hg), increased age ($\geq$60 years of age), a family history of glaucoma, diabetes, hypertension, myopia, and the use of corticosteroids. In certain embodiments, such subjects exhibit a normal IOP (11-21 mm Hg).

In other aspects, the results from the assays of the invention can be used to initiate or design a regimen of treatment, based on an increased risk for developing glaucoma. Such treatment may include one or more of the following: surgical or laser treatments, installation of shunts, treatment with miotics (such as pilocarpine, carbachol, physostigmine, demecarium, and isofluorophate), treatment with carbonic anhydrase inhibitors (such as acetazolamide and methazolamide), adrenergic agonists (such as epinephrine, dipivefrine, and α2-specific agonists such as apraclonidine), β-blockers (such as betaxolol and metipranolol), prostaglandin analogs, and osmotic diuretics.

In yet other aspects, the present invention relates to one or more oligonucleotide molecules that are amplification primers and/or extension primers for use in the present invention. Preferably, the extension primers comprise sequences selected from the group consisting of SEQ ID NOS: 1-4, and the amplification primers comprise sequences selected from the group consisting of SEQ ID NOS: 5-8. Preferably, the oligonucleotide molecules of the present invention are purified, and most preferably substantially pure molecules.

As used herein, the term "purified" in reference to oligonucleotides does not require absolute purity. Instead, it represents an indication that the sequence is relatively more pure than in the natural environment. Such oligonucleotides may be obtained by a number of methods including, for example, laboratory synthesis, restriction enzyme digestion or PCR. A "purified" oligonucleotide is preferably at least 10% pure. A "substantially purified" oligonucleotide is preferably at least 50% pure, more preferably at least 75% pure, and most preferably at least 95% pure.

In further aspects, the present invention also relates to kits for performing the methods described herein. Preferably, such kits contain one or more extension primers in an amount sufficient to perform at least one assay for determining the presence or absence of a particular polymorphic form of TIGR in a sample. More preferably, such kits contain extension primers in an amount sufficient to perform at least one assay for determining the presence or absence of at least two, and most preferably at least four, different polymorphic forms of TIGR in a sample. Preferably, the extension primers comprise sequences selected from the group consisting of SEQ ID NOS: 1-4. In certain embodiments, the kits also contain amplification primers in an amount sufficient to perform a PCR amplification of the polymorphism region(s) of interest in the assay. Preferably, the amplification primers have sequences selected from the group consisting of SEQ ID NOS: 5-8. In certain other embodiments, the kits may also contain an instruction manual providing instructions for use of the extension probes, and amplification probes if present in the kit.

The summary of the invention described above is non-limiting and other features and advantages of the invention will be apparent from the following detailed description of the invention, and from the claims.

BRIEF DESCRIPTION OF THE FIGURES

FIG. 1 represents the sequence of TIGR exon 3 (SEQ ID NO.: 9).

FIG. 2 represents the sequence of TIGR promoter (SEQ ID NO.: 10).

DETAILED DESCRIPTION OF THE INVENTION

The invention is drawn to assays that are predictive and/or diagnostic for glaucoma. In particular, the invention provides methods and compositions for determining the presence and sequence of variant alleles of genes encoding TIGR.

TIGR Polymorphisms

In a normal diploid eukaryote, each gene has 2 loci, i.e., 1 gene copy at the same locus (position) on each of 2 matched chromosomes. Different versions of a gene can occur at any locus, and these versions are called alleles. Each allele may be the wild-type (normal) allele or an allelic variant. Thus, two different versions of a TIGR gene will be present in any particular subject.

By "allelic variant" it is meant a variation in a nucleotide sequence, such as a single nucleotide polymorphism (SNP) or any other variant nucleic acid sequence or structure (e.g., duplications, deletions, inversions, insertions, translocations, etc.) in a gene encoding a gene that alters the activity and/or expression of the gene. Allelic variants and/or over- or under-express the polypeptide encoded by the gene, and/or express proteins altered activities by virtue of having amino acid sequences that vary from wildtype sequences.

Often, more than one allelic variant exists and persists in a population of individuals. By "exist and persist" it is meant that the frequency of incidence of a rare allele(s) is greater than can be explained by recurrent mutation alone (i.e., typically greater than 1%). However, the frequency of any variant allele may vary over time due to such factors as genetic drift and the like. When 2 or more different alleles of a gene are present in a population, the gene or the protein it encodes is said to be polymorphic. As used herein, a "polymorphism" refers to a specific form of a gene or protein.

Various forms of the TIGR gene can signal varying risks of developing POAG, and/or varying severity of the disease. For example, the MT-I mutation can be associated with greater visual field loss, elevated IOP, and refractoriness to conventional medical therapy compared to POAG patients not exhibiting this polymorphism. In the case of the T377M mutation, reported glaucoma rates for carriers are 100% by the age of 44. Similarly, for the K423E polymorphism, reported glaucoma rates for carriers are 10% by age 19, 74% between age 20 and 40, and 90% at age 40 or older; and for the N480K polymorphism, 25% by age 19, 50% by age 26, 75% by age 32, and 95% by age 57. The following table indicates the prevalence of each of these mutations in the population of POAG patients:

| Mutation | Prevalence |
| --- | --- |
| MT-1 | 17% |
| T377M | 0.12 |
| E423K | 0.4 |
| N480K | 0.81 |

The following additional allelic variants have been described in the TIGR gene:
TYR430HIS;
GLY357VAL;
GLN368TER;
PRO370LEU;
ILE477SER;
PRO370LEU;
GLY367ARG;
GLN337ARG;
ARG46TER; and
CYS433ARG.

Screening for TIGR Polymorphisms

The invention can provide rapid and simultaneous screening for large numbers of samples and/or for several polymorphisms of TIGR. In an exemplary aspect, the assays of the invention are designed to screen for 4 polymorphic loci of the TIGR gene; however, the skilled artisan will understand that the methods described herein could be expanded to provide screening for numerous additional TIGR polymorphic loci.

The screening methods described herein are discussed in reference to polymerase chain reaction ("PCR") amplification of genomic sequences. The skilled artisan will understand that numerous methods are known in the art for amplification of nucleic acids, and that these methods may be used either in place of, or together with, the disclosed PCR steps. Nucleic acid amplification methods, such as PCR, isothermal methods, rolling circle methods, etc., are well known to the skilled artisan. See, e.g., Saiki, "Amplification of Genomic DNA" in PCR Protocols, Innis et al., Eds., Academic Press, San Diego, Calif. 1990, pp 13-20; Wharam et al., Nucleic Acids Res. 2001 Jun. 1;29(11):E54-E54; Hafner et al., Biotechniques 2001 Apr;30(4):852-6, 858, 860 passim; Zhong et al., Biotechniques 2001 Apr;30 (4):852-6, 858, 860 passim.

In embodiments where RNA (e.g., TIGR hnRNA or mRNA) is to be screened, amplification can be carried out using a combined reverse transcription-polymerase chain reaction (RT-PCR) amplification, in which a single enzyme catalyzes the primer extension both from the initial genomic RNA template (i.e. reverse transcription) and from the DNA templates synthesized in the amplification process.

Nucleic acids, including the TIGR sequence of interest, may be isolated from biological samples through the use of routine methods. Various commercial nucleic acid purification kits, such as QIAGEN® BioRobot™ and QIAamp® 96 VIRUS kit are known to the skilled artisan, and used to isolate nucleic acids.

In various embodiments, TIGR coding sequences and/or upstream regulatory sequences are amplified prior to analysis by primer extension methods, preferably using PCR. Suitable forward and reverse primer sequences should flank the polymorphism region of interest. Exemplary primers for two regions of the TIGR gene are as follows:

| Primer Name | Primer Sequence | |
|---|---|---|
| TIGRe3F (exon 3) | 5'-gcg gtc cca aaa ggg tca gtg tat ggt gtg tgg atg cga g-3' | (SEQ ID NO.: 5) |
| TIGRe3R (exon 3) | 5'-gcg gtc cca aaa ggg tca gta agt tgt ccc agg caa aga g-3' | (SEQ ID NO.: 6) |
| TIGRmt1F (promoter) | 5'-gcg gtc cca aaa ggg tca gtg cga ata gag cca taa act ca-3' | (SEQ ID NO.: 7) |
| TIGRmt1R (promoter) | 5'-gcg gtc cca aaa ggg tca gta tct ggg gaa ctc ttc tca g-3' | (SEQ ID NO.: 8) |

Amplification primer sequences may comprise a 3' end that ensures hybridization to the target site, and may also include additional nucleotides added to the 5' end that need not participate in specific binding. Thus, such amplification primers may extend for 15 to 75 nucleotides in length, preferably 17 to 50 nucleotides in length, and more preferably from 20 to 30 nucleotides in length, only a subset of which is an exact complement to the target sequence of interest. In these embodiments, the exact complement may extend for at least 15 nucleotides, more preferably for at least 17 nucleotides, and most preferably for at least 20 nucleotides to ensure specific hybridization of the amplification primer.

Once amplified, the PCR products are treated, e.g., with Shrimp Alkaline Phosphatase (SAP) and Exonuclease I, to remove excess dNTPs and PCR primers. This is followed by a single nucleotide primer extension SNaPshot reaction (Lindblad-Toh et al., Large-scale discovery and genotyping of single-nucleotide polymorphisms in the mouse. Nature Genet. 2000 April;24(4):381-6). In this reaction, an oligonucleotide primer is designed to have a 3' end that is one nucleotide 5' to a specific point mutation site or to a specific sequence found at a boundary of a mutation that occurs at a larger scale (e.g., a duplication, deletion, inversion, etc.). The primer hybridizes to the PCR amplicon in the presence of fluorescently labeled ddNTPs and a DNA polymerase. The polymerase extends the primer by one nucleotide, adding a single, labeled ddNTP to its 3' end. Each dideoxynucleotide (e.g., ddATP, ddGTP, ddCTP, ddTTP, ddUTP, etc.) is differently labeled, e.g., each is labeled with a different fluorescent colored dye. The primers are tagged with varying lengths of nonspecific polynucleotides (e.g., poly-GACT) to allow multiplex detection of 5 or more, preferably 10 or more, and most preferably 100 or more different mutations (polymorphisms) in a single reaction. Excess ddNTPs are removed from the reaction mixture by SAP treatment. The products are fluorescently labeled oligonucleotides, each one of which may be detected, for example using an automated DNA sequencer (e.g., ABI PRISM 3100 Genetic Analyzer) based on its size (determined by electrophoretic mobility) and/or its respective fluorescent label.

Suitable extension primers for several polymorphism genotypes are as follows:

| Polymorphism | Primer Name | Primer Sequence | |
|---|---|---|---|
| MT-1 | SNP32 | 5'-cga ata gag cca taa act caa agt ggt aat aa-3' | (SEQ ID NO.: 1) |
| T377M | SNP33Δ | 5'-ccg tat tct tgg ggt ggc tac a-3' | (SEQ ID NO.: 2) |
| K423E | SNP34Δ3 | 5'-ctc aaa cct ggg aga caa aca tcc gt-3' | (SEQ ID NO.: 3) |
| N480K | SNP35Δ | 5'-gac tgc tat aag tac agc agc atg att gac tac aa-3' | (SEQ ID NO.: 4) |

EXAMPLES

The following examples serve to illustrate the present invention. These examples are in no way intended to limit the scope of the invention.

Example 1

Preparation of Biological Samples

Biological samples and other specimens are obtained, stored and prepared for assay using protocols that may vary depending on the type of sample that is to be used in the assay.

1.1 Obtaining Specimens

Any biological sample containing TIGR nucleic acids may be a suitable sample. For genomic DNA, a convenient sample can be obtained by rinsing the mouth with water to remove loose particles, followed by scraping the cheek to collect buccal epithelial cells.

Example 2

Instruments and Equipment

The following commercially available instruments and equipment are non-limiting examples of those that may be used to practice the invention. Those skilled in the art will be able to determine other instruments and equipment that may be used in the methods of the invention.

2.1 Pipettes

Standard pipettes are used to deliver volumes ranging from 0.5 to 100 mL. For volumes less than 1 ml, pipettors such as the P-10, P-20, P-200, P-1000 (Rainin Instruments, LLC) pipettors are used. Pipet tips are selected from Barrier Pipet Tips (Robbins Scientific); Pipet Tips, 20 µl and 250 µl (Beckman), and ART (aerosol resistant tips) for P-10, P-20, P-200, P-1000) (Rainin).

2.2 Electrophoresis

Examples of apparatuses that may be useful for electrophoresis and visualization are an agarose gel electrophoresis apparatus, such as CBS Scientific horizontal mini-gel; a power supply having a constant voltage of 200V or better variable power supply for electrophoresis, such as the Bio-Rad Model 200; photodocumentation apparatus, such as the Alpha Innotech Alphalmager or Polaroid DS34 t; and a transilluminator, e.g., a VWR Model LM-20E or equivalent.

2.3 Centrifugation

Centrifugation is carried in BIOMEK® 2000 or Vortex (VWR; G-560) instruments and centrifuges for spinning PCR trays (Sorvall T6000D). The 96-well-plate centrifugation system from Qiagen may also be used. Microcentrifuges such as those from Eppendorf are used with Microcentrifuge tubes (from, e.g., National Scientific, CN065S-GT).

2.4 PCR Containers and Reaction Plates

For DNA amplification (PCR), 2 ml MicroTubes with screw caps (Sarstedt; 72.693-005) may be used. A variety of 96-well plates suitable for PCR and other manipulations can be used. In the Examples herein, ABI MicroAmp Optical 96-well Reaction Plates (P/N#N801-0.0560) are used with ABI 96-well Plate Septa (P/N#4315933), or Microseal 96-well PCR microplates (MJ Research, MSP-9601) are used with Microseal A sealing film for microplates (MJ Research, MSA-5001). A 96-place storage system exemplified by VWR #30128-330, is used to store plates containing samples between steps in the assay.

2.5 PCR Cycler

A PCR cycler capable of processing 96-well plates is used in the Examples. Exemplary PCT thermal cyclers include the GeneAmp 9600 (Perkin-Elmer) or the PTC 200 (MJ Research). The MJR PTC 200 has features that are desirable regardless of which instrument is used: heating rates of up to 3° C./second, which reduce reaction times, and rapid temperature homogeneity (e.g., ±0.4° C. within 30 seconds at 90° C.). The heating block that is used may be, for example, VWR's Heat Block (VWR, 13259-007).

2.6 Automated Laboratory Workstation

In order to process a large number of samples, a multipurpose automated or semi-automated programmable workstation is used (Meldrum, Automation for Genomics, Part One: Preparation for Sequencing, Genome Research, 10:1081-1092, 2000; Meldrum, Automation for Genomics, Part Two: Squencers, Microarrays, and Future Trends, Genome Research, 10:1288-1303, 2000). Preferred features of the workstation include the ability to rapidly and accurately pipette, dilute and dispense small volumes of liquids. The exemplary programable workstation used herein is the BIOMEK® 2000 (Beckman Coulter, Inc.).

2.7 Capillary Electrophoresis DNA Sequencer

For high throughput of PCR products, an automated capillary electrophoresis (CE) system is used in order to separate labeled DNA molecules in a size-dependent manner, so that signals corresponding to each nucleotide in a sequence are detected in a sequential fashion. For reviews of the use of CE in DNA sequencing and polymorphism analysis, see Heller, Electrophoresis 22:629-43, 2001; Dovichi et al., Methods Mol Biol 167:225-39, 2001; Mitchelson, Methods Mol Biol 162:3-26, 2001; and Dolnik, J Biochem Biophys Methods 41:103-19, 1999. In the Examples, the ABI PRISMS® 3100 Genetic Analyzer is used with an ABI PRISM 3100 capillary array, 36-cm (P/N#4315931). This provides a multi-color fluorescence-based DNA analysis system that uses capillary electrophoresis with 16 capillaries operating in parallel to separate labeled PCR products. A CE DNA sequencer/analyzer that operates 96 capillaries may be preferable in assays wherein 96-well plates are used. Analyzers with the capacity to process 96 wells include the MegaBACE™ 1000 DNA Analysis System (Molecular Dynamics, Inc and Amersham Pharmacia Biotech) and the 3700 DNA Analyzer from (Perkin-Elmer Biosystems).

Example 3

Reagents 3.1 Stock Reagents

The following exemplary stock reagents are used and are stable for the indicated times when stored at the indicated temperature/conditions.

3.1.1 Agarose, SeaKem GTG (FMC 50074). Store ambient (18° C.-26° C.), stable for 1 year.

3.1.2 dNTP set, ultrapure, 100 mM solution (Pharmacia 27-2035-01). Store at −10° C. to −30° C., stable for 1 year.

3.1.3 EDTA, disodium (Sigma E-5134). Store ambient (18° C.-26° C.), stable for 1 year.

3.1.4 Ethidium bromide (Life Technologies 15585-011). Store ambient (18° C.-26° C.), stable for 1 year.

3.1.4 Ficoll (Sigma, Cat. #F2637). Store at 18-25° C., stable for 1 year.

3.1.5 Bromophenol Blue (Sigma, cat. #B6131). Store at 18-25° C., stable for 1 year.

3.1.6 Xylene Cyanol (Kodak, cat. #1B72120). Store at 18-25° C., stable for 1 year.

3.1.7 0.5 M EDTA, pH 8.0 (Amresco, cat. #E177), Store at 18-25° C., stable for 1 year.

3.1.8 Taq Extender PCR additive (Stratagene 600148) stored at −20° C., stable for 1 year.

3.1.9 If a commercially available DNA extraction kit is not used, reagents for the Proteinase K or phenol-chloroform extraction method should be prepared as is known in the art.

3.1.10 ABI 3100 POP-4 polymer (P/N4316335), stable for 1 year when stored at 2 to 10° C.

3.2 Stock Solutions

The following exemplary stock solutions are used and are stable for the indicated times when stored at the indicated temperature/conditions.

3.2.1 Water, molecular biology grade (BioWhittaker 16-001 Y or equivalent) stored ambient (18° C.-26° C.), stable for 1 year.

3.2.2 6× Gel loading dye (no xylene cyanol)

3.2.3 100 mM disodium EDTA pH 8.0

3.2.4 6%-12% (w/v) Ficoll 400

3.2.5 0.25% (w/v) bromophenol blue 3.2.6 10×TBE buffer 3.2.6.1 Prepare as 890 mM Tris Base, 890 mM Boric Acid, and 20 mM Disodium EDTA 3.2.6.2 TBE buffer (Amresco 0658 or equivalent) stored ambient (18° C.-26° C.), stable for 1 year.

3.2.7 ABI 10×Buffer (P/N402824), stored at 2 to 10° C., stable for 1 year.

3.2.8 ABI Hi Di Formamide (P/N4311320). Stored at −10° C. or colder, stable for 1 year or until the indicated expiration date.

3.2.10 100×TE buffer (Sigma T-9285 or equivalent) stored ambient (18° C.-26° C.), stable for 1 year.

3.2.11 ABI 5× Sequencing Buffer, PE Applied Biosytems, (P/N4305603), stored at −15° C. to −25° C., stable for 1 year.

3.3 Kits

The following exemplary kits may be used and are stable for the indicated time when stored at the indicated temperature/conditions.

3.3.1 ABI SNAPshot multiplex kit (P/N4323161), stored at −10 to −30° C., stable for 6 months 3.3.2 HotStarTaq™ PCR Core Kit (Qiagen 203203 or 203205) (HotStarTaq™ enzyme, 25 mMg++, M10×buffer & 5×Q Solution), stable for 1 year when stored at −10° C. to −30° C.

3.4 Enzymes

The following exemplary enzymes may be used and are stable for the indicated time when stored at the indicated temperature/conditions.

3.4.1 Shrimp Alkaline Phosphatase (USB Corporation, P/N70092X), stable for 6 months when stored at −10 to −3° C.

3.4.2 Exonuclease I (USB Corporation, P/N70073X), stable for 6 months when stored at −10 to −30° C.

3.5 Standards

The following exemplary standards may be used and are stable for the indicated time when stored at the indicated temperature/conditions.

3.5.1 DNA ladder, 50 bp (Pharmacia Biotech 27-4005-01) stable for 1 year when stored at −20° C.

3.5.2 ABI GeneScan-120 LIZ Size Standard (P/N4322362), stable for six months when stored at 2 to 10° C.

3.6 PCR Amplification Primers

Oligonucleotides used as PCR primers were prepared by Operon Technologies, Inc. (0.05, 0.2 or 1.0 micromole scale synthesis, no HPLC purification) and stored as 100 µM stocks at −10° C. or colder, conditions under which they are stable for 1 year. Table 2 gives the sequences of PCR primers used in the Examples.

3.7 Primer Extension Primers

Primer extension primers were prepared by Operon Technologies, Inc. (0.05, 0.2 or 1.0 micromole scale synthesis, HPLC purification): stored as 100 µM stocks at −10° C. or colder, stable for 1 year. The sequences of primers used in the examples are shown in SEQ ID NOS.: 1-4.

3.8 Working Stocks for PCR, Primer Extension, and SAP Treatment 3.8.1 5× Primer Mix for TIGR Duplex PCR is prepared according to the following recipe and is stable for 1 year when stored at −70° C.

| Primer (100 µM) | Volume | [5X] | [working] |
|---|---|---|---|
| TIGRe3F | 384 µl | 2 µM | 0.400 µM |
| TIGRe3R | 384 µl | 2 µM | 0.400 µM |
| TIGRmt-1F | 384 µl | 2 µM | 0.400 µM |
| TIGRmt-1R | 384 µl | 2 µM | 0.400 µM |
| H2O: | 17664 µl | | |
| Total: | 19200.0 µl | | |

3.8.1.2 TIGR PCR Master Mix is prepared according to the following recipe.

| Components | Per Rxn (µL) | ×3000 (µL) |
|---|---|---|
| 10X Qiagen PCR Buffer | 2.5 | 33000 |
| 25 mM dNTP mix | 0.25 | 7500 |
| 5X primer mix | 5.0 | 15000 |
| 25 mM MgCl₂ | 1.0 | 3000 |
| H2O | 11.0 | 33000 |
| Total | 19.75 | 59250 µL |

3.8.4 SAP+Exo I Cocktail

Combine 5 µl of SAP (1 unit/µl) and 0.2 µl of Exo I (10 unit/µl) in 1×SAP buffer to a final volume of 15 µl per reaction. The SAP+ExoI Cocktail is prepared fresh before each use.

| | Concentration | Volume (µl) for 120 rxns (full plate) |
|---|---|---|
| SAP | 1 unit/µl | 600 |
| Exo I | 10 unit/µl | 24 |
| 10x SAP buffer | 10x | 240 |
| Sterile H20 | | 936 |
| Total | | 1800 |

3.8.5 Primer Extension Primer Mix is prepared according to the following recipe.

| Primer | Concentration (µM) | Volume of primer added (1 rxn) | Volume of primer added (200 rxns) |
|---|---|---|---|
| SNP32 (MT-1) | 100 | 0.005 µL | 10 µL |
| SNP33Δ (T377M) | 100 | 0.02 µL | 40 µL |
| SNP34Δ3 (K423E) | 100 | 0.02 µL | 40 µL |
| SNP35Δ (N480K) | 100 | 0.02 µL | 40 µL |
| dH2O | | 0.935 µL | 1870 µL |
| Total: | | 1.0 µL | 2000 µL |

The mix is prepared in 15 ml sterile conical tubes and dispensed in 1 to 1.5 ml aliquots per microcentrifuge tube and stored at −70° C. or colder.

3.8.6 SNaPshot Primer Extension Master Mix

Combine 2.5 µL of ABI SNaPshot Ready Mix, 2.5 µL of 5× sequencing buffer, 1 µL of Primer Extension Primer Mix and 1 µl Sterile H₂O to a final volume of 7 µl per reaction. The Mix is prepared fresh before each use, and kept on ice until used.

| Reagent | Per Well | Per Plate |
|---|---|---|
| SnaPshot Ready Mix | 2.5 μL | 280 μL |
| 5X sequencing buffer | 2.5 μL | 280 μL |
| Extension Primer Mix | 1 μL | 112 μL |
| DH$_2$O | 1 μL | 112 μL |
| Total | 7 μL | 784 μL |

3.8.7 Second SAP Cocktail:

For each reaction, 1 μl of SAP (1 unit/μl) and 1 μl of water are combined to a final volume of 2 μl. The SAP cocktail is freshly prepared before each use.

3.8.8 Loading Mix: Ten (10) μl of Hi-Di Formamide and 0.5 μl GeneScan 120 LIZ Size Standard are combined to a final volume of 10.5 μl per sample. Lodging Mix is prepared fresh before each use.

| Reagent | Per Well | Per Plate* |
|---|---|---|
| Hi-Di Formamide | 10 μl | 1120 μl |
| GeneScan 120 LIZ Size Standard | 0.5 μl | 56 μl |
| Total | 10.5 μl | 1176 μl |

Example 4

Procedure 4.1 Preparation of Sample Trays

PCR master mix is prepared as described above and is used in the reaction. The following table describes a recipe that results in a sufficient volume for a full PCR plate (sample tray; 96-wells), and allows for excessive solution to enable pipetting from a trough with an 8-channel pipettor into all PCR wells.

| | 1 Rxn | Cocktail × 56 (½ plate) | Cocktail × 112 (full plate) |
|---|---|---|---|
| Master Mix | 19.75 μL | 1106 μL | 2212 μL |
| HotStarTaq | 0.25 μL | 14 μL | 28 μL |
| Buccal Swab/Qiagen DNA* | 5.0 μL (or 2.0 Qiagen DNA + 3.0 dH$_2$O) | — | — |
| Total | 25 μL | | |

If Qiagen DNA is used, add 2.0 μL DNA sample +3.0 μL H$_2$O per reaction; if a DNA sample is extracted with the phenol/chloroform method, it should be diluted in sterile water to a concentration of 8-16 μg/ml, and add 5 μL per reaction.

4.2 PCR Reactions

For automated PCR setup on the BIOMEK® 2000 robotic workstation, the PCR tray, a box of Robbins 125 μL pipet tips, a box of 20 μL pipet tips, the Qiagen sample tray and the reagent reservoir (trough) are placed at the appropriate positions on the BIOMEK® 2000 work surface. If the PCR or subsequent steps are set up manually, the same master mix recipe/digestion recipe is used, and the assay proceeds as described below without the BIOMEK® 2000, and single or multichannel pipettors and tips are used.

The master mix is added to the reagent reservoir. Eight positions at the end of the Qiagen sample tray are left open for controls. The sample tray is briefly spun down in a plate centrifuge outside of the master mix and template addition area (i.e., in a clean room). The control samples (typically, four positive and two negative controls) are placed in the appropriate positions in the sample tray.

The BIOMEK® 2000 station first pipets 20 μl of the master mix into each 0.2 ml PCR tray wells, and then adds 5 μl specimen DNA or control. The wells are tightly sealed with PCR tube caps pr Microseal A film. The sample tray is briefly (~5 s) vortexed and spun down for about 30 s in a plate centrifuge at 2,000-6,000 g (1,600 rpm in a Sorvall T6000D centrifuge).

The cycling program (below) is started on a thermal cycler such as the MJR PTC 200. When the temperature reaches >85° C., the PCR tray is placed in the thermal cycler and its lid is sealed.

The cycling parameters are:

| Step | Temperature | Time |
|---|---|---|
| 1 | 95° C. | 15 min. |
| 2 | 94° C. | 10 sec |
| 3 | 55° C. | 0.50° C./sec. Ramp |
| 4 | 55° C. | 10 sec. |
| 5 | 72° C. | 0.30° C./sec. Ramp |
| 6 | 72° C. | 15 sec. |
| 7 | 94° C. | 0.50° C./sec. Ramp |
| 8 | [Go to step 2 and repeat for 32 cycles*] | |
| 9 | 70° C. | 5 min. |
| 10 | 4° C. | Hold |

*Typically, 32 cycles is optimal, however 31-33 cycles may be used if the PCR products from 32 cycles are less than optimal.

After PCR is complete, the products may be stored refrigerated up to one week or frozen (<−10° C.) if a longer storage period is necessary, or they may be used immediately in the following procedures.

4.3 First SAP and ExoI Digestion

Digestion starts by adding 5 μl of PCR product and 15 μl of the SAP+ExoI Cocktail. The plate is sealed, vortexed and spun down in the plate centrifuge. The plate is then placed in the MJR PTC 200 thermal cycler and a cycling program is run using the following parameters.

| Step | Temperature | Time |
|---|---|---|
| 1 | 37° C. | 2 hr. |
| 2 | 75° C. | 15 min. |
| 3 | 4° C. | Hold |

Each step uses rapid (default) ramp to reach desired temperature. The SAP/ExoI-treated PCR products can be stored at 2-8° C. until use.

4.4 Primer Extension

SNaPshot Primer extension Master Mix is freshly prepared as described above, and 7 μl of the master mix is added to 3 μl of digestion product from Example 4.3. After addition of the SNaPshot Primer Extension Master Mix, each plate is immediately placed in the thermocycler and the "SNAP-SHOT" program is immediately run.

The plate should not be allowed to sit at room temperature more than 30 seconds. The plate is sealed, vortexed and spun down in the plate centrifuge. The plate is then placed in the MJR PTC 200 thermal cycler and a cycling program is run using the following parameters.

| Step | Temperature | Time |
|---|---|---|
| 1 | 96° C. | 10 sec. |
| 2 | 50° C. | 5 sec. |
| 3 | 60° C. | 30 sec. |
| 4 | | Go to step 1 24 more times. |
| 5 | 4° C. | Hold |

Each step uses rapid (default) ramp to reach desired temperature. The reaction plates are stored at 2-8° C. until use.

4.5 Second SAP Digestion

2 µl of the SAP Cocktail is mixed with 10 µl primer extension product from Example 4.4. The plate is sealed and vortexed, and then spun down in the plate centrifuge. The plate is placed in the MJR PTC 200 thermal cycler and a cycling program is run using the following parameters.

| Step | Temperature | Time |
|---|---|---|
| 1 | 37° C. | 1 hr. |
| 2 | 75° C. | 15 min. |
| 3 | 4° C. | Hold |

Each step uses rapid (default) ramp to reach desired temperature. The digestion plate is stored at −15° C. or lower until use.

4.6 Electrophoresis on ABI 3100 Genetic Analyzer

SAP-digested samples are prepared according to Example 4.5 for loading using a BIOMEK® 2000. The SNaPShot product is diluted 15-fold with water, and then 2 µl of the diluted product is mixed with 10.5 µl of the Loading Mix. The plate is covered with septa, vortexed and spun down in the plate centrifuge. The plate is heated at 95° C. for 5 minutes, then immediately placed on ice for 3 minutes or until use. The plate is spun down in a plate centrifuge to collect condensation. The plate is then assembled and loaded onto the ABI3100 Genetic Analyzer.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

The inventions illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

I claim:

1. A method, comprising:
   (a) incubating a reaction mixture comprising:
      (i) a sample nucleic acid obtained from a biological sample suspected of containing a TIGR nucleic acid sequence,
      (ii) a nucleic acid polymerase,
      (iii) one or more extension primers that specifically bind to said TIGR nucleic acid sequence if present, and that, when extended by one nucleotide at the 3' end, comprise a nucleotide indicative of one or more preselected polymorphisms in said TIGR nucleic acid sequence, and
      (iv) one or more labeled ddNTPs, under conditions such that, in the presence of said TIGR nucleic acid sequence, said extension primer(s) are distinctively labeled by addition of one of said labeled ddNTP(s) to the 3'-end of said detection primer, to generate a labeled nucleic acid corresponding to one of said preselected polymorphism(s); and
   (b) detecting a signal from said labeled nucleic acid, wherein said signal is related to a TIGR genotype present in said sample;
   wherein said sample nucleic acid is obtained by amplification of nucleic acid in said biological sample;
   wherein nucleic acid in said biological sample is amplified by a polymerase chain reaction; and
   wherein nucleic acid in said sample is amplified using one or more amplification primer sequences selected from the group consisting of SEQ ID NOS:5-8.

2. A method, comprising:
   (a) incubating a reaction mixture comprising:
      (i) a sample nucleic acid obtained from a biological sample suspected of containing a TIGR nucleic acid sequence,
      (ii) a nucleic acid polymerase,
      (iii) one or more extension primers that specifically bind to said TIGR nucleic acid sequence if present, and that, when extended by one nucleotide at the 3' end, comprise a nucleotide indicative of one or more preselected polymorphisms in said TIGR nucleic acid sequence, and
      (iv) one or more labeled ddNTPs, under conditions such that, in the presence of said TIGR nucleic acid sequence, said extension primer(s) are distinctively labeled by addition of one of said labeled ddNTP(s)

to the 3'-end of said detection primer, to generate a labeled nucleic acid corresponding to one of said preselected polymorphism(s); and (b) detecting a signal from said labeled nucleic acid, wherein said signal is related to a TIGR genotype present in said sample; and wherein said extension primers consist of an oligonucleotide 17-50 bases in length, comprising at the 3' end a sequence selected from the group consisting of SEQ ID NOS: 1-4.

3. The method of claim 2, wherein said sample nucleic acid is obtained by amplification of nucleic acid in said biological sample.

4. The method of claim 2, wherein said nucleic acid in said biological sample is amplified by a polymerase chain reaction.

5. The method of claim 1 or 2, wherein step (b) comprises separating said labeled nucleic acid(s) by electrophoresis.

6. The method of claim 5, wherein said electrophoresis is capillary electrophoresis.

7. The method of claim 1 or 2, wherein steps (a) and (b) are performed by automated means.

8. The method of claim 1 or 2, wherein said labeled ddNTPs are fluorescently labeled.

9. The method of claim 1 or 2, wherein said labeled ddNTPs comprise ddCTP, ddGTP, ddATP and ddTTP, each of which are physically distinguishable from one another.

10. The method of claim 9, wherein said labeled JdNTPs comprise ddCTP, ddGTP, ddATP and ddTTP, each comprise a different fluorescent label.

11. The method of claim 1 or 2, wherein said biological sample is a human sample.

12. The method of claim 11, wherein said human sample is obtained by scraping within the buccal cavity.

13. A method of identifying a subject at increased risk for developing primary open angle glaucoma, comprising correlating a TIGR genotype of said subject identified by the method of claim 1 or 2 to a relative risk of developing primary open angle glaucoma associated with said TIGR genotype.

14. A method of selecting a treatment regimen for a subject, said method comprising selecting said treatment regimen to be compatible with a TIGR genotype of said subject identified by the method of claim 1 or 2.

* * * * *